United States Patent
Reinhardt et al.

(10) Patent No.: US 10,347,386 B2
(45) Date of Patent: Jul. 9, 2019

(54) ELECTRODE COMPRISING AN EMBEDDED LAYER, AND A METHOD FOR PRODUCING SAME

(75) Inventors: Holger Reinhardt, Kempen (DE); Klaus-Peter Anhalt, Rhumspringe (DE); Lucien Opitz, Springe (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 1286 days.

(21) Appl. No.: 14/117,123

(22) PCT Filed: May 4, 2012

(86) PCT No.: PCT/EP2012/001925
§ 371 (c)(1),
(2), (4) Date: Mar. 24, 2014

(87) PCT Pub. No.: WO2012/152418
PCT Pub. Date: Nov. 15, 2012

(65) Prior Publication Data
US 2014/0209351 A1    Jul. 31, 2014

(30) Foreign Application Priority Data

May 12, 2011 (DE) .................... 10 2011 101 583

(51) Int. Cl.
*A61B 5/04* (2006.01)
*H01B 1/00* (2006.01)
(Continued)

(52) U.S. Cl.
CPC ............. *H01B 1/00* (2013.01); *A61N 1/0452* (2013.01); *A61N 1/0492* (2013.01); *H01B 13/0036* (2013.01)

(58) Field of Classification Search
CPC ............. A61B 5/0006; A61B 5/04087; A61B 5/04085; A61B 5/6833; A61B 5/0402; A61B 5/6832; A61N 1/04; A61N 1/0484
(Continued)

(56) References Cited

U.S. PATENT DOCUMENTS 3,964,469 A * 6/1976 Manley ................ A61B 5/0408
600/392
4,082,087 A * 4/1978 Howson ............. A61B 5/04085
600/391
(Continued)

FOREIGN PATENT DOCUMENTS

CN    101028521 A    9/2007
CN    101077423 A    11/2007
(Continued)

OTHER PUBLICATIONS

Ramakrishna et al. "Electrospun nanofibers: solving global issues" materials today. vol. 9 No. 3. Mar. 2006.*
(Continued)

*Primary Examiner* — Joseph A Stoklosa
*Assistant Examiner* — Brian M Antiskay
(74) *Attorney, Agent, or Firm* — Holland & Hart, LLP

(57) ABSTRACT

An electrode for transcutaneously transmitting electronic signals with a first layer that is designed to retain a liquid, also at least as a result of a capillary force, and an electrically conductive polymer layer, which contains conductive particles. The first layer is partially permeated by the polymer layer such that it protrudes out of said polymer layer on at least one first side. The first layer is designed to retain a liquid, also at least as a result of a capillary force, and the electrode includes an electrode contacting layer which is
(Continued)

partially embedded in the polymer layer, such that it protrudes out of the polymer layer on a second side opposite the first side.

20 Claims, 2 Drawing Sheets

(51) Int. Cl.
*A61N 1/04* (2006.01)
*H01B 13/00* (2006.01)

(58) Field of Classification Search
USPC .................. 600/372, 382–393, 508–509
See application file for complete search history.

(56) References Cited

U.S. PATENT DOCUMENTS

| | | | | |
|---|---|---|---|---|
| 4,300,575 | A * | 11/1981 | Wilson | A61N 1/0456 607/152 |
| 4,777,954 | A * | 10/1988 | Keusch | A61B 5/0408 600/392 |
| 5,123,423 | A | 6/1992 | Scharnberg | |
| 5,330,527 | A * | 7/1994 | Montecalvo | A61B 8/4281 252/500 |
| 5,985,990 | A * | 11/1999 | Kantner | A61L 15/58 424/448 |
| 6,032,064 | A * | 2/2000 | Devlin | A61B 5/04004 600/372 |
| 6,038,464 | A * | 3/2000 | Axelgaard | A61B 5/04087 600/391 |
| 6,263,226 | B1 * | 7/2001 | Axelgaard | A61B 5/04087 600/391 |
| 8,386,009 | B2 * | 2/2013 | Lindberg | A61B 5/0245 600/386 |
| 9,220,436 | B2 * | 12/2015 | Sandmore | A61B 5/0478 |
| 2006/0052683 | A1 * | 3/2006 | Parker | A61N 1/04 600/372 |
| 2006/0094946 | A1 * | 5/2006 | Kellogg | A61B 5/14514 600/347 |
| 2006/0116565 | A1 * | 6/2006 | Axelgaard | A61N 1/0452 600/391 |
| 2007/0049814 | A1 | 3/2007 | Muccio | |
| 2009/0209840 | A1 * | 8/2009 | Axelgaard | A61N 1/0452 600/391 |
| 2012/0190965 | A1 * | 7/2012 | Schaerer | A61B 5/0059 600/411 |
| 2013/0115837 | A1 * | 5/2013 | Kitchen | D04H 3/016 442/60 |

FOREIGN PATENT DOCUMENTS

| | | |
|---|---|---|
| DE | 2830219 A1 | 1/1980 |
| DE | 9316259 U1 | 2/1994 |
| DE | 102005058850 A1 | 6/2007 |
| DE | 102009013470 A1 | 10/2010 |
| DE | 102009017179 A1 | 12/2010 |
| EP | 0467966 A1 | 1/1992 |
| EP | 1021986 A2 | 7/2000 |
| GB | 2432323 A | 5/2007 |
| WO | 0102052 A2 | 1/2001 |

OTHER PUBLICATIONS

PCT International Search Report for PCT International Patent Application No. PCT/EP2012/001925, dated Jul. 31, 2012.

* cited by examiner

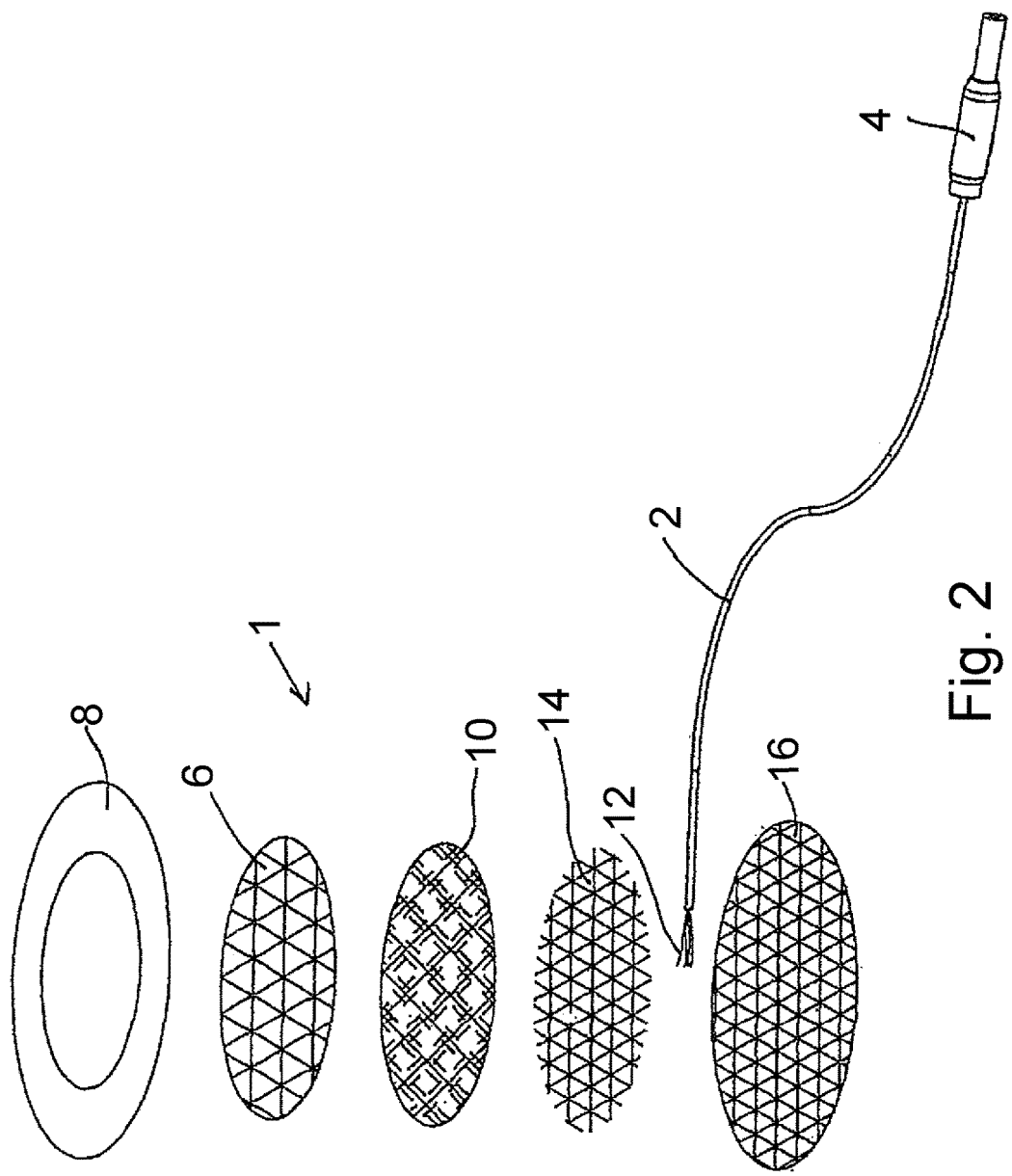

ELECTRODE COMPRISING AN EMBEDDED LAYER, AND A METHOD FOR PRODUCING SAME

TECHNICAL FIELD

The invention relates to an electrode for transcutaneously transmitting electronic signals with a first layer and an electrically conductive polymer layer containing conductive particles, the first layer being partially permeated by the polymer layer such that it protrudes out of said polymer layer on at least one first side, as well as a method for producing such an electrode as well as a bandage with this type of electrode.

BACKGROUND

These types of electrodes are used for various clinical applications, for example electro cardiograms, electro encephalograms or electromyograms, but also for more long-term processes. These types of electrodes are thus used particularly for muscle stimulation, for example building up muscle by means of functional electrical stimulation (FES) or transcutaneous electrical nerve stimulation (TENS).

In this process, electrical signals are transmitted via the electrodes to the body of the person wearing the electrodes, such that the muscles are stimulated into movement. Alternatively, it is also possible for these types of electrodes to receive electrical signals from a muscle or the skin of the wearer and supply them for further processing.

In order to enable the transmission of electrical signals from the electrode to the body of the patient, it is necessary that the actual contact between the electrode and the patient's skin occurs via an ionically conductive medium. Only the conduction of electrical signals from the patient's skin is also possible via metallic electrodes, for example. To this effect, it is known from DE 10 2009 013 470 A1 to arrange a gel cushion with an ionically conductive liquid gel on the side of the skin facing the electrode. On the other side of the gel cushion is a liquid-tight support material for preventing the liquid gel from escaping on this side of the electrode. In order to guarantee as good an electrical contact as possible between the electrode, in particular the liquid gel in the gel cushion, and the wearer's skin, a film of gel or moisture must be formed on the patient's skin. The electrodes equipped with this hydro or liquid gel are very sticky, thereby providing a good grip on the wearer's skin, at least for a short time. In contrast, sponge electrodes become damp and greasy due to the liquid that is easily squeezed out of them.

The contacting of the ionically conductive gel cushion occurs via a metal plate or a rubber electrode. This comprises a metal snap fastener on the side facing the gel cushion with which contact can be made with an ECG device, for example, by means of its cable.

In this process, the metal plate must be in constant contact with the gel cushion in order to guarantee an electrical contacting.

A similar electrode construction is known from EP 1 021 986 A2, for example. This also contains a gel body on one of the sides of a support material facing the skin, which is filled with a conductive gel. A metallic sensor with a snap fastener connecting element is arranged on the gel cushion by means of which contact can be made with the sensor, and thereby the gel cushion. In this case the metallic sensor must also be in constant contact with the gel cushion in order to guarantee an electrical contacting.

EP 0 467 966 B1 describes an electrical stimulus electrode: in this case, the electrical signals are sent directly to the patient's skin by means of a conductive cloth. This conductive cloth comprises an arrangement of conductive fibers and is soaked with a conductive adhesive that, in this case, provides the actual contact between the electrode and the skin.

All electrodes mentioned until now are unsuitable for longer use, for example with longer treatments in the form of muscle stimulations, which often last for several days. Over the course of this period an intense movement of the skin occurs at the point of the electrodes, due to muscle contraction for example, caused by the electrical signals that are introduced into the human body by the electrodes. In addition to this, the patients move a lot over the course of several days, such that high demands are put on the electrodes in terms of mechanical resistance.

Firstly, it is a disadvantage that the gel cushions described until now are very sticky, due to the liquid gel contained within them. Should a relative movement between the skin and the electrode stuck to it now occur, as a result of movements made by the patient, the adhesive point may become detached and stick to a new point the next time the patient moves. This leads to skin irritations and is generally uncomfortable for the wearer. In addition, this type of detachment and reattachment of the electrode has the disadvantage that the electrical contact between the electrode and the patient's body is broken for at least a short period, or it is at least effected. Secondly, the relative movement between the patient's skin and the electrode may cause the electrode to move, such that its optimal position relative to the muscle that it stimulates can no longer be guaranteed or a deformation of the electrode may occur.

Alongside the self-adhesive gel cushion, contacting via a metallic sensor also has disadvantages. As a result of the intense movement that one electrode on the human body is subjected to over a period of time, the contacting may be broken, such that in the worst case, the electrical contact is interrupted and thus no more current signals can be introduced into the patient's body. This would result in the failure of the therapy.

An item of clothing is described in WO 01/02052 A2 that comprises at least two different zones, one of which is designed to be electrically conductive. Both types of fabric are sewn or knitted together. The electrically conductive zones can then be used as an electrode for medical applications.

U.S. Pat. No. 5,123,423 describes a pad for defibrillators that is attached between the defibrillator electrode and the patient's skin. Due to the emergency situation in which they are used, these pads do not have an enhanced level of wearer comfort. The pads comprise a lower layer that is made from a conductive polymer. A fibrous layer, for example made from carbon fibers, is arranged in and above this, which prevents the polymer layer from also sticking to the defibrillator electrode.

In US 2007/0049814 A1 a set of clothing items is described which has electrodes and gel reservoirs, through which electrical signals can be transmitted to stimulate the wearer's muscles that are located beneath the item of clothing.

DE 93 16 259 U1 describes an electrode which is made from a conductive polymer layer and a cover layer which covers the polymer layer. The polymer layer is poured into a recess of a foam layer in order to achieve a flush joint between the conductive and non-conductive material layers.

In DE 10 2009 017 179 A1 a device for electromyostimulation is described that is made from a suit comprising one or several parts into which integrated textile-based electrodes, moisturizers and electrical leads are incorporated.

SUMMARY

The invention thus aims to propose an electrode and a method for producing such an electrode that guarantees that the patient is comfortable whilst simultaneously ensuring an optimal contacting, even during intense movement and a long period of use.

The invention solves the problem at hand by means of an electrode according to the preamble of claim 1 for the transcutaneous transmission of electrical signals, said electrode comprising a first layer that is designed to retain a liquid, at least also as a result of a capillary force, and an electrically conductive polymer layer which contains conductive particles, the first layer being partially permeated by the polymer layer such that it protrudes out of said polymer layer on at least one first side. In addition, the electrode also has a an electrode contacting layer according to the invention, that is at least partly pushed through by the polymer layer so that it sticks out of one of the first sides of the opposite side of the polymer. A connecting wire or other electrical contact is preferably arranged on this electrode contacting layer in order to supply the process with electrical signals absorbed by the electrodes or to lead electrical signals to the electrodes, which should be transmitted from the electrode to the patient.

The first layer preferably refers to a nonwoven, in particular a nano nonwoven. Since the first layer is designed to retain a liquid, also at least as a result of a capillary force, the disadvantages caused by the use of a hydro gel cushion are effectively reduced. A sponge or a nonwoven, in particular a micro or nano nonwoven, may be used as a first layer. The smaller the openings and cavities in the first layer, the greater the resulting capillary strength, thereby increasing the first layer's capacity for retaining the liquid. The capillary strength is particularly high during the use of micro and nano nonwovens. It is often completely sufficient to only lightly moisten the first layer, for example, as this moisture in the first layer is very strongly bound by the very high capillary strength of a nano nonwoven in particular. It is even conceivable for the electrodes to be designed such that they can be used when dry, and sufficient moisture coming only from sweat found on the patient's skin can enter the first layer of the electrode, in order to provide an electrically conductive connection.

The utilization of a nano nonwoven as a first layer has been proven to be an especially preferable arrangement, as has just been demonstrated. With the aid of an example embodiment with a nano nonwoven the invention will be described in the following. All of the embodiments which are relevant for the nano nonwoven are also applicable for first layers made from other materials. If a nano nonwoven is thus discussed in the following, it also refers to a first layer that may be present in another arrangement.

The nano nonwoven, which can be produced particularly by means of an electrospinning method, forms the contact surface on the patient's skin. Should the nonwoven be produced using an electrospinning method, for example, very thin fibers develop, for example made from a polymer solution as a result of treatment in an electric field. Typically, fibers with a diameter of less than 1000 nm develop, meaning that this case involves nano nonwovens. A nonwoven of this type comprises a number of small and very small gaps. The capillary effect is so strong in these gaps, as a result of the very small diameter, that a liquid held within them is mechanically and physically bound and stored in the nonwoven. Should the nano nonwoven now be soaked with a liquid containing ions, the nonwoven becomes ionically conductive, even if the actual nonwoven material should be electrically insulating. Should an electrical voltage be supplied, the ions flow to the corresponding point, thereby creating a current flow.

Due to the fact that the strong capillary effect in the nano nonwoven causes the water or liquid containing ions to be physically bound more strongly than with other materials and considerably impeded during evaporation, hygroscopic additives need not be used, so that this nano nonwoven is not sticky. The disadvantages of the hydrogel or liquid gel cushion known from the prior art, which implicated a constant replacement and sticking of the electrode, are hereby effectively avoided. The combination of a nonwoven and an ionically conductive medium guarantees an optimal contacting to the skin of the person wearing the electrode. As the electrodes according to the embodiment of the present invention do not stick to the skin, it is also possible to reach an optimal contacting with body parts that may be subjected to intense movement, such as knees or elbows, during intense movement of these areas without causing the skin to tense or the electrode to partially detach.

The nano nonwoven is partially permeated by a polymer layer that contains conductive particles. However, this does not refer to ionically conductive particles, but electronically conductive particles in which the current flow materializes as a result of a movement of the electrons. Due to the fact that the nano nonwoven is partially permeated by the polymer layer, the polymer containing the conductive particles infiltrates the small and very small gaps in the nano nonwoven in this area. However, since the nano nonwoven is only partially permeated by the polymer layer, only a part of the gaps in the nano nonwoven is permeated and filled by the polymer. The remaining gaps can be filled with the liquid containing ions. This results in an optimal contacting between the ionically conductive liquid in the nano nonwoven and the electronically conductive particles in the polymer layer. Preferably one third to one half of the nano nonwoven is surrounded by the polymer, while the rest of the nano nonwoven protrudes out of the polymer layer on the side of the electrode facing the skin. If the nano nonwoven has a thickness of 370 μm, for example, the penetration depth is 130 μm.

The nano nonwoven, such as an electrospun nanofiber, as well as the polymer layer are pliably and flexibly formed, such that the entire electrode construction as described above is also flexible and pliable. This guarantees that this type of electrode can easily reproduce movements made by the body or the muscles underneath the skin without causing the electrode to detach or move relatively to the body of the person wearing the electrode. This ensures that, independent from the type and strength of the movement of the wearer, an optimal contacting is guaranteed, such that an optimal therapy or control can take place by means of the signals transmitted to, or absorbed from, the body by the electrodes.

Moreover, the electrode contacting layer is partially surrounded by the polymer layer, as with the nano nonwoven, and is embedded in it. However, the electrode contacting layer also protrudes out of the polymer layer on the side of the polymer layer facing the skin, i.e. the side opposite the nano nonwoven.

It has been proven to be especially advantageous if the electrode contacting surface comprises a layer made from a conductive textile. This may refer to a textile coated with a metal, in particular silver.

The use of this type of metallically coated textile has a range of advantages. Firstly, this layer is pliable and flexible, such that the electrode construction can still follow the patient's body movements without the resulting mechanical strain having an effect on an electrical contacting. Furthermore, a connecting wire can be attached to this type of coated textile in a particularly advantageous way.

This type of metallically coated textile has a number of individually coated fibers, each of which can work as an individual power line. Due to the large number of fibers and hence power line channels, it is irrelevant for the contacting if some of these contacts are no longer electrically conductive, for example due to broken or chipped metallic coating. Should the connecting wire now be placed on this type of textile, such as a fabric, a number of contacts occur between the various strands of the connecting wire and the fibers of the covered fabric or textile. It is also therefore irrelevant if a certain proportion of these contacts becomes detached, breaks or no longer works because of other influences, and no longer conducts the electric current. Contacting is still guaranteed as, in principle, it is sufficient for the conduction by means of the flow of electrons if one of the contacts remains intact. In this way, a very stable contacting is achieved, particularly against the mechanical strain, without restricting the movability, flexibility and elasticity of the electrode.

Alternatively, the electrode contacting layer may also comprise a metallic ink printed on a carrier film, in particular a silver ink. The number of contacts between the printed pattern and, for example, a connecting wire arranged thereon or its strands can be controlled via the choice of pattern. For example, if a filigree and widespread pattern is used, a number of contacts can also be created in this way, of which only a small proportion need function in order to guarantee an optimal contacting of the electrode.

In a particularly advantageous embodiment, the electrically conductive polymer layer contains conductive pigments, electrically conductive carbon black, graphite, CNTs or dendritic metallic particles as conductive particles. CNT stands for carbon nano tubes. In particular, the use of combinations of plate-shaped and almost spherical particles has proved effective. In this way, the percolation threshold can be exceeded particularly safely and simply with a relatively low filling level, thereby causing an electrical conductivity throughout the entire polymer layer.

In particular, the use of conductive pigments has the additional advantage that the color of the electrode can be freely selected as a result. Electrodes for different purposes have various properties, such as various electrical conductivities. In this way, for example, an electrode for absorbing electrical signals from the patient's skin is equipped with a higher electrical conductivity than an electrode through which electrical signals should be transmitted to the skin. Should the conductivity of the polymer now be produced by using graphite or carbon black, for example, the color is set in this way. A visual difference in the various electrodes for the different application areas is therefore not possible. Once the electrode is removed from the packaging, the user is no longer able to determine for which purpose the electrode is intended. Should an electrode for absorbing electrical signals now be used inadvertently as a stimulation electrode, it may lead to an overly strong current flow due to the increased conductivity when a voltage of the same value is in use, which is uncomfortable for the wearer. In particular it can lead to pain and a burning sensation.

By using conductive particles in the polymer layer, carbon black or graphite need not be used. In general, carbon black or graphite are made up of nano particles so small that they can enter the human body. In addition, they may get into the air as a result of abrasion and enter into the human body via the respiratory tracts or similar. The potential dangers coming from these nano particles are safely avoided by using conductive particles which, for example, have a size within the micrometer range. Additionally, it is also possible to develop the electrodes according to aesthetic aspects, for example by using conductive pigments.

The use of conductive pigments in the conductive polymer layer means the color of this polymer layer can be freely selected, so that the color of the user's electrode can indicate whether it is an electrode for absorbing electrical signals or, for example, a stimulation electrode with which electrical signals should be transmitted to the patient's skin. This prevents incorrect usage.

A method according to the invention for producing this type of electrode comprises the following steps:

a) Moulding or spreading at least a first part of a conductive polymer layer made from a polymer that contains conductive particles,
b) Pushing a first layer, such as for example nonwoven, in particular a nano nonwoven into the polymer layer, such that the first layer is partially permeated by the polymer layer and protrudes out of said polymer layer on a first side.

The polymer is poured onto a work surface while it is in a fluid and workable state. There is the option, as an addition or alternative, to create a homogenous layer by coating, in which the conductive particles, in particular pigments, are arranged in a preferred direction. As long as it is in this state, the nano nonwoven is now laid on the polymer layer and pushed into said polymer layer. If necessary, there is a small waiting period between the two steps so the polymer layer can harden a little. Alternatively, the viscosity of the polymer layer can also be selected in such a way that the first layer, for example the nano nonwoven, can be pushed into it immediately. This makes it possible to determine the exact scale of the penetration depth of the first layer into the polymer layer.

The method preferably comprises the following next steps:

c) Allowing the at least first part of the conductive polymer layer to harden,
d) Moulding or spreading a second part of the conductive polymer layer on a second side of the polymer layer that is opposite the first side and
e) Pushing an electrode contacting layer into the second part of the polymer layer, such that the electrode contacting layer is partially embedded in said polymer layer and protrudes out of the polymer layer on the second side.

After the first layer, for example the nano nonwoven, has been pushed into the first part of the conductive polymer, the polymer is left to harden to the point that the two layers, i.e. the nano nonwoven and the conductive polymer layer can be moved together, in particular reversed. Following the reversal, a second part of the conductive polymer layer can be arranged on the now upper, formally the under, side of the first part of the conductive polymer layer. This is also arranged when it is in a fluid state, such that an electrode contacting layer that is, for example, in the form of a conductive textile can be pushed into this second part. In this case the penetration depth of the electrode contacting layer into the polymer layer and its protrusion out of the polymer can also be set precisely. A connecting wire, particularly with several strands, can subsequently be arranged on the electrode contacting layer, such as the metallically covered conductive textile, in order to guarantee the optimal contacting at the greatest possible number of points.

A self-adhesive, electrically insulating textile may then be stuck on the side of the electrode facing the skin when it is in use, i.e. the side on which the electrode contacting layer protrudes out of the polymer layer. This prevents the formation of undesirable contacts, such as contact with the patient's clothes.

The conductive particles that can be used for the conductive polymer layer comprise in particular dendritic metallic particles, preferably silver, electrically conductive carbon black, graphite, CNTs or conductive pigments. These may consist of a mica plate and a core mica sphere, for example, which may be covered with a tin oxide layer that is doped with antimony. In particular the combination of plates and spheres as additional particles has been proven effective in simply and safely exceeding the percolation threshold.

All disadvantages of the prior art are overcome with an electrode according to the invention. The electrode does not stick to the patient's skin, meaning that uncomfortable detachment and reattachment that may be caused by movement does not occur. In addition, the flexible and elastic construction of the electrode ensures that the electrical contacting remains secure, even with a strong mechanical strain. This is especially true for arrangements in which a connecting wire is, for example, fixed onto a metallically conductive textile. The large number of various contact points means that the connection is unsusceptible to mechanical strains.

It is advantageous if the at least first part of the conductive polymer layer is moulded on an electrode contacting layer. It is thereby possible to produce an electrode according to an embodiment of the present invention easily, quickly and cost-effectively. This particularly prevents one part of the conductive polymer layer from being poured and/or coated twice, since the entire polymer layer can be applied in one step.

It is possible to determine how far the electrode contacting layer should be permeated by the applied polymer layer via the viscosity of said polymer layer. It can also be simultaneously determined how far the first layer, which is applied later, should penetrate the already fixed fluid polymer layer. The viscosity of the polymer layer can be determined via the proportion of solvents within the layer or via additives, for example. The penetration depth can additionally be regulated via the contact pressure with which one layer is laid onto the layer below.

In particular, if a nonwoven, such as a nano nonwoven, is used as a first layer, it is possible to produce this from a polymer that also corresponds to the base polymer of the conductive polymer layer. In this case it is especially simple to create a connection between the nano nonwoven acting as a first layer and the polymer layer made from a conductive polymer: for example, the polymer layer is applied to a work surface. It is hardened slightly until the proportion of solvents still present in the polymer layer reaches a predetermined value. The nano nonwoven made from the polymer is then applied to the polymer layer. The nonwoven is also slightly dissolved by the solvents contained in the polymer layer, such that it can be joined with the polymer layer, which is also dissolved. This case is called cold welding. This enables a particularly good connection between the individual layers.

As demonstrated, nano nonwovens in particular are produced by means of electrospinning. As the conductive polymer layer refers to an electrically conductive layer, it is possible to spin the nano nonwoven directly onto this electrically conductive layer. This also makes it possible to eliminate some steps in the procedure, thus accelerating the whole method and thereby reducing the production costs.

Should the unhardened polymer of the applied polymer layer be used for this procedure, the described cold welding connection is simultaneously created, such that a particularly good connection between the individual layers is achieved, alongside the simple, quick and cost-effective production.

An electrode according to an embodiment of the present invention may be used particularly in a bandage. A bandage according to the invention thus comprises at least one of the described electrodes. Electrodes according to the present invention can be designed in such a way that they do not stick to the patient's skin by themselves. Therefore a bandage presents a good possibility to set the position of the electrodes on the patient's body without irritating the skin. It has been proven to be especially advantageous if the at least one electrode is arranged on one strap of the bandage such that it can be detached by means of, for example, a velcro fastener. This makes it possible to detach the electrode from the bandage after use, for example once the therapy is complete, and if necessary, to use it on another bandage for a completely different body part. These types of electrode can thus be used for a long time and, if required, on different body parts for various therapies on different patients.

BRIEF DESCRIPTION OF THE DRAWINGS

With the aid of a drawing an embodiment of the present invention will be explained in more detail. It shows:

FIG. 2—an electrode according to an embodiment of the present invention in an exploded diagram.

DETAILED DESCRIPTION

Figure 1:
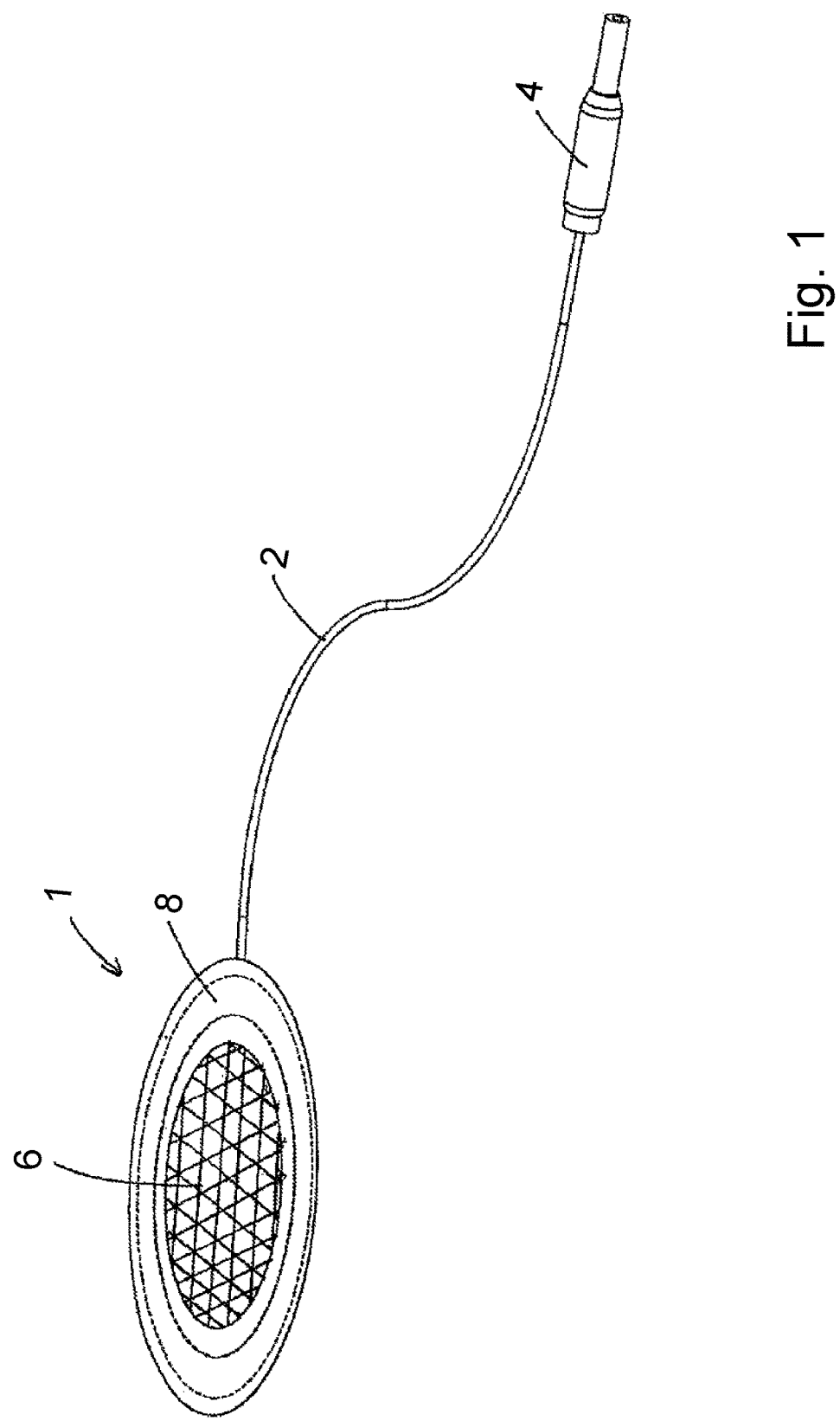
FIG. 1—a schematic diagram of an electrode according to a first embodiment of the present invention.

FIG. 1 shows an electrode according to a first embodiment of the present invention. A connecting wire 2 can be recognized, on whose end a connector 4 is arranged. This can be used to connect it, for example, to an electric control system or another device that processes electrical signals taken from the electrode 1 or sends electrical impulses through the connecting wire 2 to the electrode 1, in order to transmit them to the patient. Other forms of the electrical contacting that are particularly compatible with existing devices, such as ECG, EEG and EMG, can also of course be provided in place of the embodiment shown in FIG. 1.

The electrode 1 is located on the end of the connecting wire 2 facing the connector 4. In the middle area of the electrode 1 a nano nonwoven 6 can be seen, which comes into contact with the skin of a patient when the electrode 1 is in use. A film 8 is located around this contact area that may be made from polyurethane, for example. In the embodiment shown, this is provided to restrict the electrode surface, by means of which electrical signals can be transmitted to the skin, and simultaneously prevent a conductive polymer layer 10, situated beneath the nano nonwoven 6, from coming into contact with the patient's skin.

The geometric form of the electrode can be selected completely freely and can be adapted to the desired currents or voltages, the body parts on which the electrode should be used, and other individual conditions.

FIG. 2 shows the electrode depicted in FIG. 1 in an exploded view. It is again possible to see a connecting wire 2 on whose end the connector 4 is located. The other end is not connected to the electrode 1 in FIG. 2. The individual strands 12 can be seen, which protrude out of the connecting wire 2. The actual electrode 1 is shown to be made from five different layers. The polymer layer 10 is found on the middle, which comprises conductive particles. In this case it is important that the form and number of the particles is selected in such a way that the percolation threshold is exceeded, such that the electrical current can be conducted through the entire polymer layer 10.

The nano nonwoven 6 is situated above the polymer layer 10. In the completed state, the electrode 1 is partially located within the polymer layer 10, thus creating an optimal contacting between the two layers. In this case, the nano nonwoven 6 is soaked with a liquid that contains ions. Consequently, this refers to an ionically conductive material by means of which the electrical signals can be transmitted to the skin of a patient particularly effectively. In FIG. 2, as in FIG. 1, the film 8 can be seen above the nano nonwoven; the film may be made from polyurethane, for example. On the one hand, this again restricts the electrode surface via which the electrical impulses can be transmitted to the skin, and on the other hand, prevents a direct contact between the polymer layer 10 and the skin. The polymer layer 10 with the conductive particles found within it refers to an electron conductor. The current flow in this layer is therefore achieved via the transport of electrons and not the transport of ions, as is the case in the nano nonwoven 6. A direct contact between the polymer layer 10 and the patient's skin may consequently be uncomfortable and painful for the patient. If this kind of contact can be safely prevented in another way, the film 8 is redundant.

In FIG. 2 an electrode contacting layer 14 is depicted beneath the polymer layer 10, which may be in the form of a conductive textile, for example. In this case, metal may be deposited via evaporation onto the textile or used to coat said textile so that it becomes electrically conductive. This type of textile, for example in the form of a coated fabric, possesses a number of possible electrical conducts and channels. By placing the strands 12 of the connecting wire 2 on the electrode contacting layer, a great number of contacts are formed, all of which are capable of conducting the electric current from the connecting wire into the electrode contacting layer 14. Should some of these contacts now fail due to mechanical strain or production errors, it does not cause the contacting to tear. This further guarantees the functioning of the electrode 1 and ensures that electrical signals, for example, can be transmitted to the wearer's body.

In FIG. 2 a layer of an electrically insulating textile 16 forms the closing. This prevents electrical contact from occurring between the electrode contacting layer 14 and, for example, the patient's clothing, which may have a disruptive influence on the electrical signals to be transmitted.

In order to produce this type of electrode 1, a part of the polymer layer 10 is first of all poured in its fluid state and, if necessary, spread to form a surface. The first layer is pushed into this fluid polymer of the polymer layer 10, the first layer perhaps being in the form of the nano nonwoven 6, which may be in the form of an electro spun fiber. The penetration depth of the nano nonwoven 6 into the polymer layer 10 can be precisely determined via the pressure and/or viscosity of the polymer layer, which may be controlled by means of the solvent content, such that it can also be determined how far it protrudes out of the polymer. This enables an optimal contacting. In a further step, the polymer is hardened to the point that it can be moved with the nano nonwoven 6 within it. In particular, it can now be reversed so that the nano nonwoven 6 is situated beneath the first part of the polymer layer 10. A second part of the polymer layer 10 is now poured onto the slightly hardened first part of the polymer layer 10; the electrode contacting layer 14, for example in the form of a metallically covered textile, is also pressed into said second part when it is in a fluid state. This layer is also pushed into the fluid polymer of the polymer layer 10, such that the penetration depth of the layer in the polymer and its protrusion out of said polymer can be optimally determined.

Following another step in the method, once the two polymer layers 10 have hardened to the point that the electrode 1 can be processed further, the connecting wire 2 with its strands 12 can be laid, according to the design of the electrode, on the electrode contacting layer 14, which is now connected with the polymer layer 10. This results in the numerous electrical contacts described above, so that the failure of some of these contacts does not incur the complete failure of the electrode.

The invention claimed is:

1. An electrode for transcutaneously transmitting electronic signals, comprising:
   a first layer arranged and configured to contact a person's skin;
   an electrically conductive polymer layer containing conductive particles, the first layer being only partially permeated by the electrically conductive polymer layer such that the first layer protrudes out of the electrically conductive polymer layer on a first side, the first layer being designed to retain a liquid at least as a result of a capillary force;
   an electrode contacting layer, which is partially embedded in the electrically conductive polymer layer, such that the electrode contacting layer protrudes out of the electrically conductive polymer layer on a second side opposite the first side;
   a polyurethane film arranged to contact the person's skin and to prevent the polymer layer from coming into contact with the person's skin.

2. The electrode according to claim 1, wherein the first layer comprises a nonwoven material.

3. The electrode according to claim 2, wherein a connecting wire is arranged on the electrode contacting layer.

4. The electrode according to claim 1, wherein the electrode contacting layer comprises a layer of conductive textile.

5. The electrode according to claim 4, wherein the conductive textile is a textile that is coated with a metal.

6. The electrode according to claim 1, wherein the electrode contacting layer comprises a metallic ink printed onto a carrier film.

7. The electrode according to claim 1, wherein the electrically conductive polymer layer contains conductive pigments, graphite, electrically conductive carbon black, CNTs or dendritic metallic particles that act as conductive particles.

8. A bandage with at least one electrode according to claim 1.

9. The bandage according to claim 8, wherein the at least one electrode is arranged on one strap of the bandage such that the at least one electrode can be detached.

10. An electrode for transcutaneously transmitting electronic signals, comprising: a first side;
a second side opposite the first side;
an electrically conductive polymer layer containing conductive particles; a liquid retaining layer configured to retain liquids through a capillary force, the liquid retaining layer being only partially permeated by the electrically conductive polymer layer such that the liquid retaining layer protrudes out of the electrically conductive polymer layer on at least the first side, the liquid retaining layer arranged and configured to contact a person's skin, the liquid retaining layer comprising a nano nonwoven material;
an electrode contacting layer only partially embedded in the electrically conductive polymer layer and protruding out of the electrically conductive polymer layer on the second side.

11. The electrode according to claim 10, further comprising a connecting wire arranged on the electrode contacting layer.

12. The electrode according to claim 10, wherein the electrode contacting layer comprises a layer of conductive textile.

13. The electrode according to claim 12, wherein the conductive textile is coated with metal.

14. The electrode according to claim 13, wherein the metal is silver.

15. The electrode according to claim 10, wherein the electrode contacting layer comprises a silver ink printed onto a carrier film.

16. The electrode according to claim 10, wherein the electrically conductive polymer layer comprises at least one of conductive pigments, graphite, electrically conductive carbon black, CNTs and dendritic metallic particles that act as conductive particles.

17. An electrode for transcutaneously transmitting electronic signals, comprising: a first side;
a second side opposite the first side;
an electrically conductive polymer layer containing conductive particles, the conductive particles being sized in a micrometer range of about 1 micron:
a liquid retaining layer configured to retain liquids through a capillary force, the liquid retaining layer being only partially permeated by the electrically conductive polymer layer such that the liquid retaining layer protrudes out of the electrically conductive polymer layer on at least the first side, the liquid retaining layer arranged and configured to contact a person's skin;
an electrode contacting layer only partially embedded in the electrically conductive polymer layer and protruding out of the electrically conductive polymer layer on the second side.

18. The electrode according to claim 17, wherein the liquid retaining layer comprising a nano nonwoven material.

19. The electrode according to claim 17, wherein the electrode contacting layer comprises a layer of conductive textile.

20. The electrode according to claim 17, wherein the electrically conductive polymer layer comprises at least one of conductive pigments, graphite, electrically conductive carbon black, CNTs and dendritic metallic particles that act as the conductive particles.

\* \* \* \* \*